United States Patent [19]
Lankinen

[11] Patent Number: 6,132,394
[45] Date of Patent: *Oct. 17, 2000

[54] MEDICAMENT CHAMBER IN AN INHALATION APPARATUS

[75] Inventor: Tapio Lankinen, Turku, Finland

[73] Assignee: Leiras Oy, Turku, Finland

[ * ] Notice: This patent issued on a continued prosecution application filed under 37 CFR 1.53(d), and is subject to the twenty year patent term provisions of 35 U.S.C. 154(a)(2).

[21] Appl. No.: 08/765,113

[22] PCT Filed: May 26, 1995

[86] PCT No.: PCT/FI95/00291

§ 371 Date: Nov. 25, 1997

§ 102(e) Date: Nov. 25, 1997

[87] PCT Pub. No.: WO95/32752

PCT Pub. Date: Dec. 7, 1995

[30] Foreign Application Priority Data

May 31, 1994 [FI] Finland .................................. 942562

[51] Int. Cl.[7] ................................................. A61M 13/00
[52] U.S. Cl. .......................... 604/58; 604/57; 128/203.13
[58] Field of Search ................................. 604/24, 57, 58, 604/59; 128/200.14, 203.12, 203.15, 203.21

[56] References Cited

U.S. PATENT DOCUMENTS

| | | | |
|---|---|---|---|
| 1,671,011 | 5/1928 | Braecklein . | |
| 2,534,636 | 12/1950 | Stirn | 128/203.15 |
| 2,603,215 | 7/1952 | Arnow | 128/206 |
| 4,274,403 | 6/1981 | Struve . | |
| 4,460,102 | 7/1984 | Barringer | 220/85 |
| 5,201,308 | 4/1993 | Newhouse | 128/203.15 |
| 5,263,475 | 11/1993 | Altermatt et al. | 128/203.15 |
| 5,315,987 | 5/1994 | Swann | 128/201.28 |
| 5,441,060 | 8/1995 | Rose et al. | 131/271 |
| 5,505,196 | 4/1996 | Herold et al. | 128/203.15 |
| 5,575,280 | 11/1996 | Gupte et al. | 128/203.15 |

FOREIGN PATENT DOCUMENTS

| | | |
|---|---|---|
| 0 052 440 | 5/1982 | European Pat. Off. . |
| 0 451 741 | 10/1991 | European Pat. Off. . |
| WO 89/01340 | 2/1989 | WIPO . |
| WO89/01348 | 2/1989 | WIPO . |
| WO 92/00771 | 1/1992 | WIPO . |
| WO 92/04068 | 3/1992 | WIPO . |
| WO 92/09322 | 6/1992 | WIPO . |
| WO 93/00123 | 1/1993 | WIPO . |
| WO 93/03782 | 3/1993 | WIPO . |

Primary Examiner—Wynn Wood Coggins
Assistant Examiner—LoAn H. Thanh
Attorney, Agent, or Firm—Marshall, O'Toole, Gerstein, Murray & Borun

[57] ABSTRACT

The invention relates to a medicament chamber (6) included in an inhalation apparatus and provided with a container (2) containing a desiccant. The chamber (6) is tightly sealed and has a moisture permeability as poor as possible, and the container (2) is permeable to moisture.

22 Claims, 2 Drawing Sheets

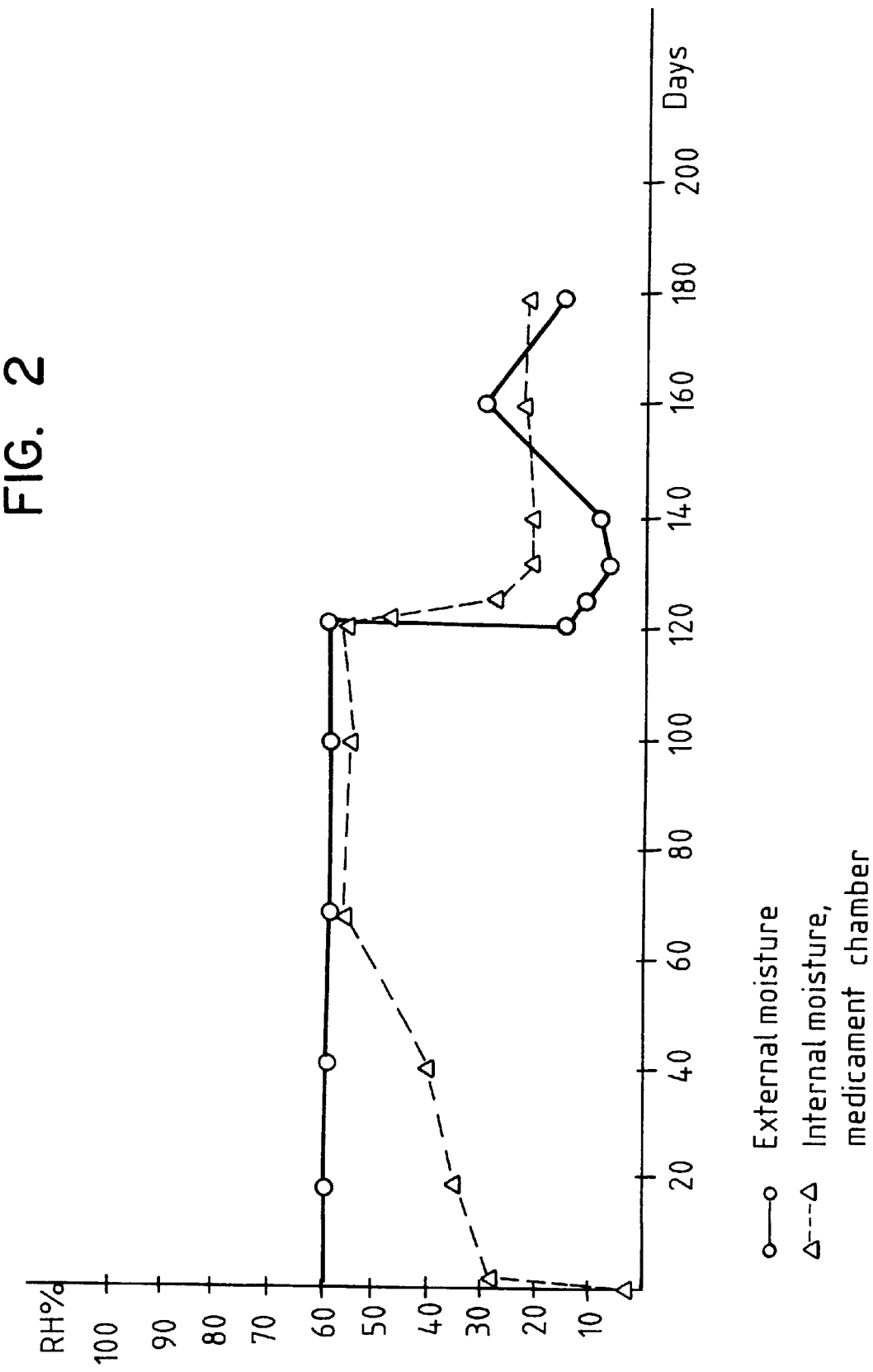

MEDICAMENT CHAMBER IN AN INHALATION APPARATUS

The present invention relates to a medicament chamber in an inhalation apparatus, including a device for the regulation of moisture.

Until recently, the commonly used inhalation apparatus has comprised a medicament mixture packed in an aerosol container for dispensing a finely powdered medicament as a spray into the respiratory organs of a patient. However, the environmental hazards produced by propellants used in aerosol containers have recently led to the development of various types of powder inhalators.

The prior known powder inhalators can be constructed such that the medicament involves the use of individual capsules or the apparatus is provided with a medicament chamber which contains a plurality of doses and is used for metering the medicament with various types of metering devices into the inhalable air. This provides a possibility of storing the medicament either in a pure non-diluted form or with some appropriate additive added therein. In order to secure the effective and reliable operation of the apparatus in view of delivering a desired amount of medicament into the airways of a user and also providing accurate metering, the powdered medicament must possess certain physical and chemical properties. Several of these properties, such as the fluidity, agglomeration, capacity, morphology or the like of a powder, are affected by moisture. Medicaments and/or additives are often hygroscopic and/or sensitive to chemical or morphological changes in high-moisture environments. Thus, operation of the apparatus can be detrimentally affected by moisture, i.e. the composition of a powder and the amount of medicine particles to be inhaled may be considerably reduced, whereby the metering or dosage will be inaccurate and dosage concentrations will be inconsistent. It should also be noted that the inhalator is often used for long periods of time and, thus, the above problems will be further pronounced.

In apparatus provided with a medicament chamber and a metering device, the above problems are also quite obvious. The prior art discloses a variety of solutions to these problems, based on fitting the inhalation apparatus with a container disclosing a desiccant e.g. silica gel. For example, the publication WO 92/09322 discloses an inhalation apparatus having its medicament chamber provided with a lid whose internal wall can be fitted with a chamber containing a desiccant. Correspondingly, in an apparatus as disclosed in the publication WO 89/01348, the inhalation chamber has its end wall fitted with a desiccant-containing compartment, the inflowing air being absorbed through said compartment.

In the device discribed in detail in U.S. Pat. No. 4,274,403, the medicament chamber is separated from the desiccant container by means of a porous layer. In these prior art devices, the desiccant is included in a capsule located in connection with a separate medicament chamber and provided with a suitable moisture-permeable wall or membrane, which thus forms a separate component in the capsule. The junctions between the membrane and the rest of the capsule may develop problems in terms of tightness and, thus, the assembly is not absolutely reliable as some of the desiccant may find its way within the medicament. This is not acceptable when the question is about an inhalation medicament.

Furthermore, in these prior known devices the desiccant container is in contact with ambient air. The desiccant must be capable of drying both the ambient air and the medicament. Thus, in order to achieve a desired drying effect, it is necessary to use a considerable excess of desiccant relative to the moisture content of the medicament.

An object of the present invention is to eliminate the above drawbacks and to provide a medicament chamber for a powder inhalator, wherein the capacity of the desiccant is only used for the elimination of internal moisture in the medicament chamber in such a manner that the desiccant and the powdered medicament are not even in a slightest contact with each other. By using silica gel or some other agent possessing a corresponding reversible dehydrating capacity as a desiccant it is possible to adjust the internal moisture of a medicament chamber to remain within a certain range regardless of the external moisture.

The invention is characterized in that the medicament chamber is tightly sealed and has as poor a moisture permeability as possible, and the container is also tightly sealed but permeable to moisture, and that the medicament chamber has a moisture permeability which is lower than that of the container, the internal moisture of the medicament chamber adjusting to a value between the moisture outside said chamber and the internal moisture of said container depending on the adsorption properties.

The chamber is provided with a removable tight lid and/or sealed inlets.

The container is preferably integral and made in a single piece, thus avoiding joints between various materials.

In order to reduce moisture and/or to maintain a desired moisture inside the medicament chamber a material having a suitable permeability is selected for constructing said container.

The regulation of moisture conditions can also be effected either by changing the material thickness of a medicament chamber or a container, by adjusting the surface area or by treating the material for changing its permeability, this involving various surface treatments, for example.

A solution according to the invention is capable of using nearly all the capacity of a desiccant for the drying of a powdered medicament, since the desiccant is only required to dehumidify the interior of a medicament chamber.

Operation of the apparatus can also be regulated by selecting suitable materials according to their moisture permeability. For example, inside a medicament chamber, the atmospheric moisture or humidity can be half of that found outside, whereby the dehydrating effect may be sufficient, yet avoiding electrostatic charges caused by excessive dryness and possibly interfering with operation of the apparatus.

Hence, operation of the apparatus is based on the fact that the medicament chamber itself and the walls of a desiccant container have different permeabilities to moisture. In a well-functioning assembly, the desiccant container is more permeable to moisture than the medicament chamber, whereby the medicament chamber has an internal moisture which is lower than the external moisture but nevertheless higher than the internal moisture of the desiccant container. If the use is made of an irreversibly moisture adsorbing desiccant, e.g. a molecular sieve, this equilibrium works until the capacity of the desiccant is fully used. Thereafter, the internal moisture of a medicament chamber strives to reach the external moisture and the properties of a powdered medicament may change rapidly during moisture peaks. When an inhalator is held at a high moisture, e.g. outdoors in a rainy weather, the tests indicate that the internal moisture of a medicament chamber reaches the external moisture within a few hours.

The dehydrating properties of silica gel are reversible, such that the drying capacity depends on external moisture. When the capacity is exhausted e.g. at the 40% relative humidity, it is still capable of absorbing a considerable amount of moisture at the humidity of 60%. If the relative humidity decreases e.g. to the 20% relative humidity, silica gel delivers moisture until its capacity has reached the level consistent with the 20% external humidity. This feature can be preferably used in an apparatus of the invention for controlling the internal moisture of a medicament chamber at the time when an essential portion of the drying capacity has already been exhausted: due to reversible dehydration the internal moisture of a medicament chamber remains lower than the maximum external moisture and higher than the minimum external moisture. In view of the stability of a powdered medicament it is preferable to eliminate the moisture peaks. If, for some reason, the powdered medicament must be maintained at 10–30% relative humidity for the entire service life of an inhalator, this can be accomplished by using a sufficient amount of silica gel that has spent a part of its drying capacity.

The invention will now be described in more detail with reference made to the accompanying drawings which illustrate one embodiment of the invention.

FIG. 2 depicts the moisture content in a chamber of the invention.

Figure 1:
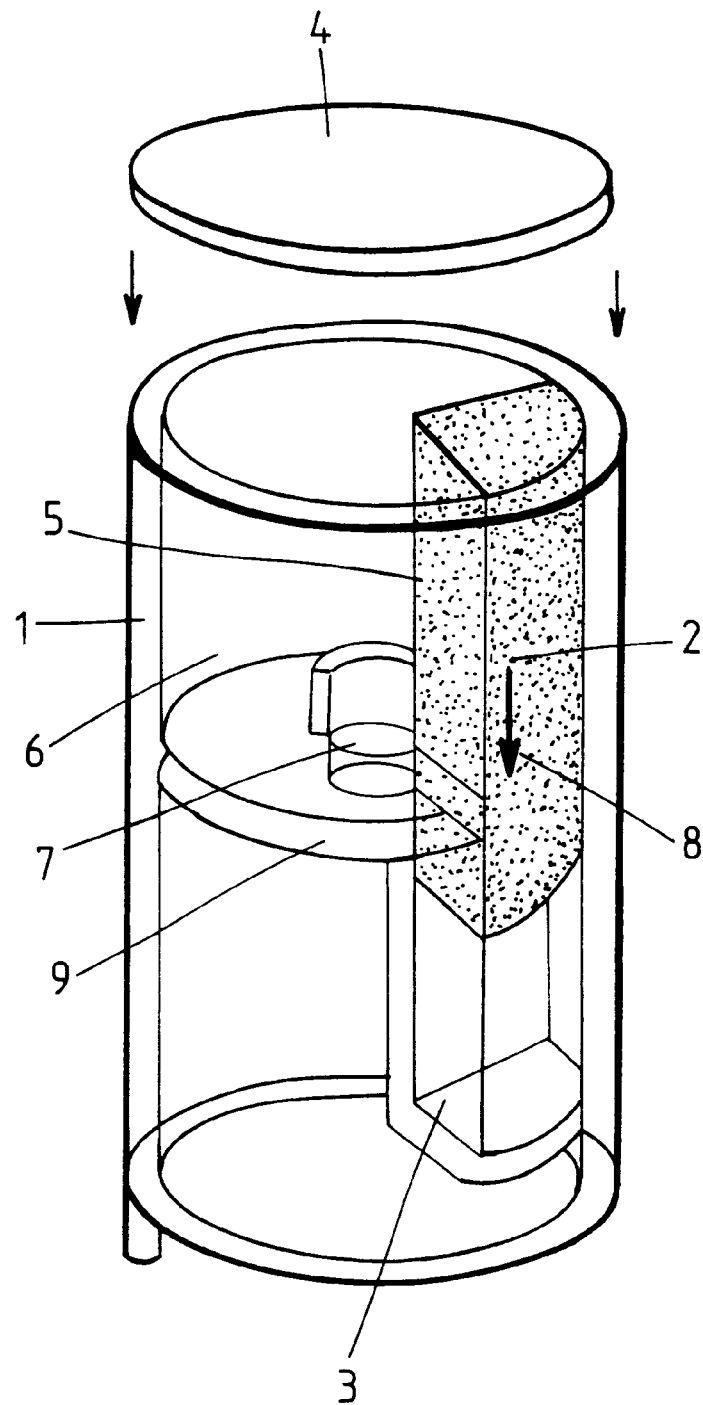
FIG. 1 shows an apparatus of the invention schematically.

Referring to FIG. 1, the inhalation apparatus is generally shown as a tubular body 1 for a powdered medicament and is provided with a metering device (not shown in detail, however). The apparatus is manufactured from a material having a poor moisture permeability, such as a suitable plastics material, e.g. polyethylene and polypropylene. The top section of the apparatus includes a medicament chamber 6, defined by a floor 9 as well as a removable and tightly sealable lid 4. In the middle of the chamber floor 9 is a sealed hole or tightly sealed inlet 7 extending through the floor as well as a collar for indicating the position of a metering device. The metering device is not illustrated in this context as it is not an essential part of the invention. The chamber is provided substantially over its entire length with a pocket 3 which is designed for a container 2 containing a desiccant.

The container 2 is set in position by pushing in the direction of an arrow 8 all the way to the bottom of the pocket 3.

The container 2 comprises a vessel made of a single material, for example polycarbonate or acrylonitrile butadiene styrene resin (ABS) or a like. As described above, the material for making the container is selected so that the container exhibits an appropriate moisture permeability, the alternatives (also in combinatation) being the material thickness, its treatment for controlling the permeability, as well as its shape or the size of its surface area exposed to the material to be dehydrated.

The container 2 is filled with a moisture absorbing agent, a desiccant, for example with silica gel, and then it is tightly sealed. This can be effected by hot sealing or it is possible to use a lid-equipped container 2, the lid 14 being tightly sealable to the container 2.

In its proper position, the container 2 is located in a medicament chamber which is sealed relative to ambient air. In addition, the container is in contact with a medicament but, due to the tightness of the container, there is no risk of a desiccant mixing with the medicament.

FIG. 2 is based on test results depicting operation of the apparatus with silica gel as a desiccant. When using 0.7 g of desiccant and 0.5 g of medicament, the apparatus has been kept 120 days at 60% relative humidity and at 40° C., the penetration of moisture being accelerated relative to normal conditions. The internal moisture of the medicament chamber reaches the external moisture in 70 days. When the apparatus after 120 days was transferred to room conditions, it was possible to prove the above-presented theory, according to which the internal moisture of the medicament chamber remained within the range of maximum and minimum external moisture.

What is claimed is:

1. A method for the regulation of moisture within a medicament chamber (6) included in an inhalation apparatus comprising the steps of:

providing a medicament chamber:

providing a separate desiccant container (2) disposed in an interior of said chamber containing a desiccant, and providing said medicament chamber made from a material having a moisture permeability which is lower than the moisture permeability of a material used for making the desiccant container (2).

2. A method for the regulation of moisture within a medicament chamber (6) included in an inhalation apparatus comprising the steps of:

providing a medicament chamber;

providing a separate desiccant container (2) disposed in an interior of said chamber containing a desiccant, and adjusting the thickness, total surface area or surface treatment for said medicament chamber (6) and said desiccant container (2) such that the medicament chamber (6) has a moisture permeability which is lower than that of the desiccant container (2).

3. A medicament chamber for an inhalation apparatus, said medicament chamber comprising:

a separate moisture-permeable desiccant container disposed in an interior of said chamber, said container (a) containing a desiccant for the regulation of moisture and (b) having a moisture permeability higher than the moisture permeability of said medicament chamber, said desiccant container being capable of adjusting the internal moisture of the medicament chamber to a value between (a) the moisture outside said chamber and (b) the internal moisture of said desiccant container, said medicament chamber being tightly sealed and having a poor moisture permeability.

4. A medicament chamber according to claim 3, further comprising an element selected from the group consisting of a removable tightly sealed lid and tightly sealed inlet.

5. A medicament chamber according to claim 4, wherein said moisture-permeable desiccant container is made from a single material.

6. A medicament chamber according to claim 5, further comprising a desiccant container made from a material having a moisture permeability higher than the moisture permeability of a material used for making said medicament chamber.

7. A medicament chamber according to claim 6, further comprising a desiccant container made from a material treated to adjust the permeability characteristics of said material.

8. A medicament chamber according to claim 20, wherein said moisture-permeable desiccant container is made from a material selected from the group consisting of polycarbonate and acrylonitrile butadiene styrene resin.

9. A medicament chamber according to claim 5, further comprising a desiccant container made from a material treated to adjust the permeability characteristics of said material.

10. A medicament chamber according to claim 9, further comprising a desiccant container made from a material having a moisture permeability higher than the moisture permeability of a material used for making said medicament chamber.

11. A medicament chamber according to claim 10, further comprising a desiccant container made from a material treated to adjust the permeability characteristics of said material.

12. A medicament chamber according to claim 4, further comprising a desiccant container made from a material treated to adjust the permeability characteristics of said material.

13. A medicament chamber according to claim 3, wherein said moisture-permeable desiccant container is made from a single material.

14. A medicament chamber according to claim 13, further comprising a desiccant container made from a material having a moisture permeability higher than the moisture permeability of a material used for making said medicament chamber.

15. A medicament chamber according to claim 14, further comprising a desiccant container made from a material treated to adjust the permeability characteristics of said material.

16. A medicament chamber according to claim 13, wherein said moisture-permeable desiccant container is made from a material selected from the group consisting of polycarbonate and acrylonitrile butadiene styrene resin.

17. A medicament chamber according to claim 13, further comprising a desiccant container made from a material treated to adjust the permeability characteristics of said material.

18. A medicament chamber according to claim 3, further comprising a desiccant container made from a material having a moisture permeability higher than the moisture permeability of a material used for making said medicament chamber.

19. A medicament chamber according to claim 18, further comprising a desiccant container made from a material treated to adjust the permeability characteristics of said material.

20. A medicament chamber according to claim 3, further comprising a desiccant container made from a material treated to adjust the permeability characteristics of said material.

21. The medicament chamber of claim 3, wherein said desiccant chamber is removable.

22. The medicament chamber of claim 21, further comprising a pocket for accepting said desiccant chamber.

* * * * *